United States Patent [19]

Lerner

[11] 4,115,590
[45] Sep. 19, 1978

[54] BINUCLEAR PHENOLS FOR REDUCING PLASMA LIPID LEVELS

[75] Inventor: Sidney I. Lerner, Cincinnati, Ohio

[73] Assignee: Ethyl Corporation, Richmond, Va.

[21] Appl. No.: 6,588

[22] Filed: Jan. 28, 1970

Related U.S. Application Data

[63] Continuation-in-part of Ser. No. 347,357, Feb. 26, 1964, abandoned.

[51] Int. Cl.$^2$ ............... A61K 31/05; A61K 31/10; A61K 31/105; A61K 31/19
[52] U.S. Cl. ............... 424/337; 424/308; 424/336; 424/339; 424/346
[58] Field of Search ............... 424/308, 336, 337, 339, 424/346

[56] References Cited

U.S. PATENT DOCUMENTS

| 2,479,948 | 8/1949 | Luten et al. | 260/620 X |
| 2,785,188 | 3/1957 | Coe | 260/620 X |
| 2,792,428 | 5/1957 | Pikl | 260/619 |
| 2,933,472 | 4/1960 | Bader | 260/47 |
| 2,940,852 | 6/1960 | Herrick et al. | 96/91 |
| 2,955,038 | 10/1960 | Smith | 96/107 |
| 2,967,774 | 1/1961 | Bell et al. | 99/163 |
| 2,987,445 | 6/1961 | Levesgue | 424/83 X |
| 3,057,926 | 10/1962 | Coffield | 260/609 |
| 3,100,229 | 8/1963 | Orloff | 260/609 |
| 3,253,042 | 5/1966 | Worrel | 260/608 |
| 3,271,456 | 9/1966 | Delanne et al. | 260/593 |
| 3,272,869 | 9/1966 | O'Shea | 260/607 |
| 3,574,853 | 4/1971 | Bernhart | 424/337 |

Primary Examiner—Albert T. Meyers
Assistant Examiner—Vera C. Clarke
Attorney, Agent, or Firm—Donald L. Johnson; John F. Sieberth; Robert A. Linn

[57] ABSTRACT

Plasma lipid levels are reduced by internally administering to a mammal a binuclear phenol. The two aromatic rings may be bonded together directly as in 4,4'-bis(2,6-di-tert-butylphenol). Likewise, the aromatic rings may be bonded through a bridging group such as —CH$_2$—CH$_2$—, —SO—, —S$_m$—, —O—CH$_2$—CH$_2$—O—, —CH$_2$—SO$_2$—, —CH$_2$—S$_n$—CH$_2$—, —CH$_2$—O—CH$_2$—, and

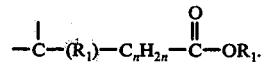

16 Claims, No Drawings

BINUCLEAR PHENOLS FOR REDUCING PLASMA LIPID LEVELS

CROSS-REFERENCE TO RELATED APPLICATION

This is a continuation-in-part of application Ser. No. 347,357, filed Feb. 26, 1964, now abandoned.

BACKGROUND AND DESCRIPTION OF THE INVENTION

In the above-mentioned parent application I disclosed that a class of phenols lowered mammalian plasma lipid levels upon internal administration of such a phenol to a mammal to be treated. This invention pertains to that subject matter and also to a preferred embodiment, use of the compound 4,4'-thio-bis(6-tert-butyl-o-cresol) which is mentioned on lines 7-8 of page 5 of the parent application. Another preferred embodiment is use of 4,4'-bis(2,6-di-tert-butylphenol) named on lines 4 and 5 of that page.

This invention relates to a method and composition for reducing plasma lipid levels and particularly cholesterol, triglyceride and phospholipid levels.

Prior to this invention there has been a great need for an effective antihyperlipemic agent which is low in toxicity and is relatively free of undesirable side effects. For example, it is believed that coronary artery disease and atherosclerosis in man are associated with an abnormally high concentration of cholesterol and other lipids in the blood stream. Of particular significance is the concentration of the $\beta$-lipoprotein fraction in the blood. The reduction of the amount of these lipids, including not only free and esterified cholesterol, but also phospholipids and triglycerides, is of major importance in the prevention and treatment of coronary artery disease, atherosclerosis other vascular and heart ailments and disorders of lipid metabolism.

It is therefore an object of this invention to provide a method for reducing plasma lipid levels, particularly cholesterol triglyceride and phospholipid levels. Another object is to provide a pharmaceutical composition capable of lowering plasma lipid levels when internally administered. Still another object is to provide such reductions without untoward side effects. A further object is to provide pharmaceutical compositions suitable for oral administration. A still further object is to provide such compositions which effectively lower the $\beta$-lipoprotein fraction of serum lipids.

According to one embodiment of this invention, the above and other objects are accomplished by providing a method of lowering plasma lipid levels which comprises internally administering a compound of this invention in an amount sufficient to lower the plasma lipid level. The compounds of this invention are as follows:

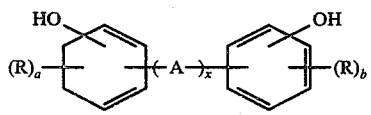

wherein: R is selected from the group consisting of alkyl, cycloalkyl, aryl and aralkyl; $a$ and $b$ are each independently selected from 0–4; $x$ is selected from 0 and 1; and A is selected from the group consisting of —CH$_2$—SO$_2$—, —SO—, —S$_m$—, —CH$_2$—S$_n$—CH$_2$—, —CH$_2$—O—CH$_2$—, —O—CH$_2$—CH$_2$—O—, and

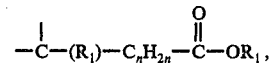

wherein $m$ is from 1–4; $n$ is selected from 0–4 and R$_1$ is selected from the group consisting of hydrogen and R.

In the above bisphenols, it is preferred that alkyl have from 1–20 carbon atoms, cycloalkyl have from 6–12 carbon atoms, aryl have from 6–12 carbon atoms and aralkyl have from 7–12 carbon atoms. The alkyl substituents may be unsaturated, for example, olefinic, but it is preferred that they be saturated, or paraffinic. Examples of such compounds include: 2,2'-bis(6-methylphenol); 2,4-diethyl-α-(3,5-diethyl-4-hydroxy-6-methylphenylsulfonyl)-o-cresol; (2-cyclohexyl-3,6-di-m-heptyl-4-hydroxy-5-isopropylphenyl) (3-ethyl-2-hydroxy-6-methyl-5-phenylphenyl)sulfide; 3-tert-amyl-2-sec-butyl-2'-ethyl-4-n-hexyl-6,4'-dihydroxy-3'-methyl-6'-propyl-biphenyl; [6-(3'-dodecyl)-3,5-diisobutyl-4-(2'-octyl)-o-cresol] [5-benzyl-3-methyl-6-p-methylcyclohexyl-4-(3'-pentadecyl)-o-cresol] disulfide; methyl 4-(2-benzyl-4-hydroxyphenyl)-4-(3-ethyl-6-m-ethylbenzyl-4-hydroxyphenyl) butyrate; n-butyl 2-(4,6-di-tert-amyl-2-hydroxyphenyl)-2-(4-n-butyl-2-ethyl-6-hydroxyphenyl) caproate; (2,6-dicyclohexyl-5-methyl-p-cresol) [2-o-ethylphenyl-3-methyl-5-phenyl-6-(di-o-isopropylphenyl)-p-cresol] ether; benzyl 4,4-bis(2-hydroxyphenyl) valerate; phenyl 3-[2-α-methylbenzyl)-5-p-ethylcyclohexyl-4-hydroxy-3-(2'-tetradecyl)-6-n-tridecylphenyl]-3-[2-(3'-decyl)-5-(4'-hexadecyl)-4-hydroxy-3,5-dimethylphenyl] butyrate; (5-ethyl-4-p-n-amylphenyl-3-phenyl-o-cresol) (3-n-hexyl-p-cresol)trisulfide; 4,4'-tetrathiobisphenol; 1-(4-hydroxy-3,6-di-p-methylphenylphenyl)-2-(3-o-n-propylcyclohexyl-6-hydroxy-5-p-methylphenyl) ethane; o-cresol(2-n-dodecyl-5-o-isopropylbenzyl-3-o-phenylcyclohexyl-p-cresol) sulfide; 2,2'-ethylenedioxybis[6-(3'-eicosyl)-4-phenylphenol]; [3-(di-o-ethylcyclohexyl)-4-hydroxy-5-methylphenyl] (2,6-dicyclohexyl-4-hydroxy-5-methylphenyl)trisulfide; (6-methyl-o-cresol) [3-tert-butyl-6-(4'-heptadecyl)o-cresol) trisulfide; [3-(α,α-diethylbenzyl]-4-hydroxy-6-m-isopropylphenyl-2-tert-octyl-5-(3'-nonyl)phenyl] [3-(α-ethyl-α-n-propylbenzyl)-4-m-n-amyl-cyclohexyl-6-hydroxy-2-methyl-5-o-sec-butylphenylphenyl] disulfide; cyclohexyl 6-phenyl-6-(2-hydroxy-6-methylphenyl)-6-[4-hydroxy-2-(4'-nonadecyl)-5-(3'-octadecyl)-6-n-propylphenyl] caproate; 4,4'-thiodiphenol; 4,4'-sulfonyldi-o-cresol; 2,2',6,6'-tetraisopropyl-4,4'-bi-3,5-xylenol; 2,2'-thiobis(4,6-di-tert-butyl-m-cresol; 4,4-bis(3-tert-butyl-4-hydroxyphenyl)valeric acid; 4,4-bis(p-hydroxyphenyl) valeric acid; and 4,4-bis(4-hydroxy-m-tolyl)valeric acid.

In another embodiment of this invention I provide a composition having anticholesterolemic and antilipemic activity comprising a suitable pharmaceutical carrier and a pharmaceutically effective amount of a compound as described above.

While the compounds described above by Formula I are all generally useful in this invention, certain structures are preferred. Preferred compounds comprise those compounds of Formula I in which the phenyl moieties are the same, each phenyl moiety containing two substituents, one of which is ortho to the hydroxyl group and the other is either in a position selected from ortho and para to the hydroxyl group or para to the first-mentioned ortho substituent. Such compounds are generally easier and more economically prepared and are more effective than the other compounds. This preferred group of compounds can be represented by a formula selected from the following two formulas:

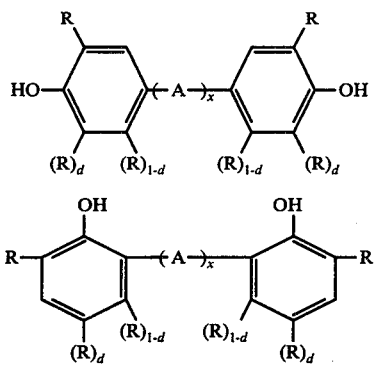

wherein R, A and x are as defined above following Formula I and d is selected from 0 and 1. Examples of such compounds include: 2,6-dimethyl-α-(3,5-dimethyl-4-hydroxyphenylsulfonyl)-p-cresol; 2,2'-thio-bis(2-sec-amyl-5-phenylphenol); α,α'-ethylenedioxybis(2-p-ethyl-cyclohexyl-5-sec-butyl-p-cresol); 4,4'-tetrathiobis[2-cyclohexyl-6-(α,β-diethyl-p-methylbenzyl)phenol]; di-[6-p-methylcyclohexyl-3-(3'-nonyl)-o-cresol] ether; α,α'-thiobis[6-(2'-heptyl)-4-p-phenylphenyl-o-cresol]; 4,4'-tetrathiobis(2,5-di-tert-butylphenol); 4,4'-bis[2-benzyl-5-(4'-eicosyl)phenol]; 6,6-bis[3-(2'-dodecyl)-2-hydroxy-5-methylphenyl] caproic acid; 4,4'-ethylenebis(2-n-hexadecyl-6-methylphenol); 2,2-bis[5-(α-methylbenzyl)-3-phenylcyclohexyl-2-hydroxyphenyl] acetic acid; 4,4'-bi-2,6-xylenol; 2,2'-thiobis(6-tert-butyl-p-cresol); 2,2', 6,6'-tetrakis(α-methylbenzyl)-p,p'-biphenol; 2,2'-sulfinylbis (6-tert-butyl-p-cresol); 4,4-bis(4-hydroxy-3,5-xylyl) valeric acid; 4,4'-thiobis)6-cyclohexyl-o-cresol]; 2,2',6,6'-tetracyclohexyl-p,p'-biphenol; and 4,4'-thiobis(6-tert-butyl-m-cresol).

The most preferred group of compounds are those of Formula II in which d is 1, one of the ortho substituents is an alkyl group of from 1–12 carbon atoms and the other substituent is an alpha-branched alkyl group of from 3–12 carbon atoms. These compounds are generally the most effective and most economically prepared. Examples of such compounds include: 2,6-di-tert-amyl-α-(3,5-di-tert-amyl-4-hydroxy phenylsulfonyl)-p-cresol; 4,4'-trithiobis(2-isopropyl-6-dodecylphenol); α,α'-dithiobis[2-(4'-dodecyl)-6-methyl-p-cresol]; di-(2-sec-butyl-6-n-octyl-p-cresol) ether; α,α'-ethylenedioxybis(2-tert-octyl-6-methyl-p-cresol); 2,2-bis(3-tert-butyl-5-ethyl-4-hydroxyphenyl propanoic acid; 4,4'-bis(2,6-di-isopropyl phenol); 4,4'-bis(2,6-di-tert-butylphenol); 4,4'-thiobis(2,6-di-tert-butylphenol; 6,6'-di-tert-butyl-4,4'-bi-o-cresol; 2,2'-di-tert-butyl-6,6'-diisopropyl-p,p'-biphenol; 6,6'-diisopropyl-4,4'-bi-o-cresol; 4,4'-thiobis(6-tert-butyl-o-cresol); α,α'-thiobis(2,6-di-tert-butyl-p-cresol); 4,4'-trithiobis(2,6-di-tert-butylphenol); 4,4'-dithiobis(2,6-di-tert-butylphenol); 4,4'-dithiobis(6-tert-butyl-o-cresol); 4,4'-ethylenebis(2,6-di-tert-butylphenol); 4,4-bis(4-hydroxy-3,5-diisopropylphenyl) valeric acid; 4,4-bis(5-tert-butyl-4-hydroxy-m-tolyl) valeric acid; α,α'-ethylenedioxybis(2,6-di-tert-butyl-p-cresol); and 2,2',6,6'-tetra-sec-butyl-p,p'-biphenol.

The compounds of this invention can be prepared by methods well known to the art. Those compounds in which the phenyl moieties are the same can be prepared by reaction of an appropriate phenol, or cresol, using a reactant which will yield the desired bridging group. With those compounds having different phenyl moieties, two different phenols or cresols can be used in the reaction and ordinary separation procedures, such as fractional distillation, crystallization and solvent extraction procedures, etc., can be used.

In those compounds where A is

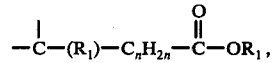

a convenient reactant is the corresponding ketonic acid or ester; for example levulinic acid can be condensed with an appropriate phenol where a valeric acid bridge, substituted on the 4 carbon atom, is desired. Where A is —O—CH$_2$—CH$_2$—O—, ethylene glycol can be condensed with an appropriate phenol. Where A is —CH$_2$—CH$_2$—, an appropriate α-iodo-cresol can be reacted, via the Wurtz reaction, with metallic sodium. Where A is —CH$_2$—O—CH$_2$—, an appropriate benzyl hydroxide can be dehydrated with, for example, sulfuric acid. Where A is —CH$_2$—S$_n$—CH$_2$—, compounds where n is 2 can be prepared by reacting an appropriate benzyl chloride with an approximately equivalent amount of Na$_2$S to form the benzyl sodium mercaptan, which can be hydrolized with, for example, dilute HCl to form the benzyl mercaptan. The benzyl mercaptan can then be mildly oxidized to form the desired disulfide. If values of n of 3 or 4 are desired, the benzyl sodium mercaptan can be reacted with SCl$_2$ or S$_2$Cl$_2$, respectively. If the monosulfide is desired, one half mole of Na$_2$S can be reacted with an appropriate benzyl chloride and the monosulfide will form. Where A is —S$_m$—, compounds where m is 1 or 2 can be prepared by reacting an appropriate phenol with SCl$_2$ or S$_2$Cl$_2$ respectively. If the trisulfide or tetrasulfide is desired, the disulfide can be converted, by mild reduction, to the corresponding mercaptan. The mercaptan can then be reacted with SCl$_2$ to form the trisulfide or with S$_2$Cl$_2$ to form the tetrasulfide. Where A is —SO— or —SO$_2$—, the corresponding thiobisphenol can be oxidized, for example, with H$_2$O$_2$ in acetone. Compounds with an —SO— bridge will be produced first and compounds with an —SO$_2$— bridge will be produced on further oxidation.

Also included as anticholesterolemic and antilipemic agents within the scope of this invention are compounds of Formula I which are substituted with one or more of the following groups; —NO; —NO$_2$; —N(R$_2$)$_2$;

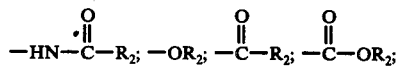

and halogen, such as Cl and Br; where R$_2$ is selected from the group consisting of hydrogen and R, R being defined above following Formula I. These substituents may be in one or more positions on the ring or one or more may be on one or more of the hydrocarbon substituents described above. Examples of such compounds include: 2,2'-thiobis(6-tert-butyl-4-methoxyphenol); 2,2'-dithiobis(6-tert-butyl-4-methoxyphenol); 2,2'-thiobis(4-chlorophenol); 2,2'-thiobis(6-tert-butyl-4-chlorophenol) and 2,2'-trithiobis(6-tert-butyl-4-chlorophenol).

The compounds of this invention effectively reduce circulating serum lipid levels using very low dosage regimens. This allows use in pharmaceutical forms which are both convenient for administration and pleasant for consumption by the patient.

To demonstrate the outstanding effectiveness of the compounds of this invention, and by way of example, tests are performed on dogs (Beagles) which are separated into four groups. The Control Group is maintained on a diet of Allied Mills - Tail Wagger Dog Food-Krums to which is added 5.0 weight per cent of a corn oil. The Experimental Groups I, II and III are maintained on the same diet as the Control Group except that a compound of this invention is added to the extent of 0.3, 1.0 and 3.0 weight per cent, based on the weight of the dog food, respectively. The compound is added by dissolving it in the corn oil up to the limit of solubility and thereafter thoroughly mixing any additional amount of compound with the dog food. After 30 days, samples of plasma and serum are taken and the serum analysed for total lipid, total cholesterol, free cholesterol and cholesterol-ester values. The serum from the dogs in the Experimental Groups are found to contain significantly less total lipid, total cholesterol, free cholesterol and ester cholesterol than the serum from the dogs in the Control Group.

After 90 days of being maintained on the above diets, dogs in the Control Group and Experimental Groups are sacrificed and their plasma and serum are analyzed for cholesterol, phospholipid and triglyceride values. The serum from the dogs in the Experimental Groups are found to contain significantly less cholesterol phospholipid and triglyceride than the serum from the Control Group.

The amount of $\alpha$- and $\beta$-lipoprotein in the serum for each group is then determined by ultracentrifugation. Serum from the dogs in the Experimental Groups are found to contain significantly less $\alpha$-lipoprotein and $\beta$-lipoprotein than serum from the Control Group.

The compounds of this invention give outstanding reductions in lipid and lipoprotein values, particularly in the $\beta$-lipoprotein values. High $\beta$-lipoprotein values are generally associated with atherosclerosis in man.

Efficacious results are also obtained using components of this invention with other mammals such as cattle, sheep, rabbits, and others, and this invention is particularly desirable for treating humans.

In contrast to antilipemic agents heretofore available, the compounds of this invention possess distinct advantages with respect to safety for human treatment and with respect to untoward side effects.

The compounds are administered internally and may be parenterally or orally administered, the latter being preferable. For oral administration, pharmaceutical preparations of this invention may be made by following the conventional techniques of the pharmaceutical chemist. These techniques involve granulating and compressing when necessary or variously mixing and dissolving or suspending the ingredients as appropriate to the desired end product. Numerous pharmaceutical forms to carry the compounds can be used. For example, the pure compound can be used or it can be mixed with a solid carrier. Generally, inorganic pharmaceutical carriers are preferable and particularly solid inorganic carriers. One reason for this is to the large number of inorganic materials which are known to be pharmaceutically safe and acceptable, as well as very convenient in preparing formulations. The compositions may take the form of tablets, linguets, powders, capsules, slurries, troches or lozenges and such compositions may be prepared by standard pharmaceutical techniques. Tablet compositions may be coated or uncoated and they may be effervescent or non-effervescent. Conventional excipients for tablet formations may be used. For example, inert diluents, such as magnesium carbonate or lactose, distintegrating agents such as maize starch or alginic acid, and lubricating agents such as magnesium stearate may be used. A preferable tablet composition is one which comprises from about 10 to about 500 milligrams of a compound of this invention.

If a liquid carrier is used, the preparation may be in the form of a soft gelatin capsule, a syrup, a liquid solution or suspension.

The hydrocarbon solubility of most of the compounds of this invention is high enough to allow the use of pharmaceutically acceptable oils as carriers. For example vegetable or animal oils such as sunflower oil, safflower oil, maize oil or codliver oil can be used. Glycerine can also be used. With this latter solvent, from 25 to 30 per cent water may be added. When water alone is the carrier, or when the solubility of the compound in the oil is low, the preparations can be administered in the form of a slurry.

Emulsion compositions may be formulated using emulsifying agents such as sorbitan tri-oleate, polyoxyethylene sorbitan monooleate, lecithin, gum acacia or gum tragacanth. Aqueous based suspensions may be prepared with the aid of wetting agents such as polyethylene oxide condensation products of alkylphenols, fatty alcohols or fatty acids and with suspending agents, for example a hydrophilic colloid such as polyvinylpyrrolidone. The emulsions and suspensions may contain conventional excipients such as sweeting agents, flowing agents, coloring materials and preservatives.

The compounds of this invention may be administered in the form of a nutritive preparation in which the active ingredient is mixed with proteins, such as casein, and carbohydrates. In addition to the active ingredient, dietary supplements such as vitamins, salts of glycerophosphoric acid, choline, inositol and amino acids such as methionine may be added.

The percentage of the compound to be used in the pharmaceutical carrier may be varied. It is necessary that the compound constitute a proportion such that a suitable dosage will be obtained and it is preferred to use pharmaceutical compositions containing at least 10 weight per cent of the compound. Activity increases with concentration of the agent in the carrier, but those compositions containing a significant amount of carrier, e.g. at least 1 per cent and preferably at least 5 per cent, are preferred as they allow for the easier administration of the compound.

For parenteral use, the compounds of this invention can be formulated with sterile ingredients, compounded and packaged asceptically. They may be administered intravenously or intramuscularly. Useful solvents for formulation in such use are the polyhydric aliphatic alcohols and mixtures thereof. Especially satisfactory are the pharmaceutically acceptable glycols, such as propylene glycol, and mixtures thereof. Glycerine is another example of a polyol which is particularly useful. Up to 25–30 per cent by volume of water may be incorporated in the vehicle if desired. An 80 per cent aqueous propylene glycol solution is a particularly convenient solvent system. A pH range, about 7.4, and isotonicity compatible with body isotonicity, is desirable. Basicity may be controlled by addition of a base as required, and a particularly convenient base is monoethanolamine. It may often be desirable to incorporate a local anaesthetic and such are well known to those skilled in the art. For example, lidocaine ($\beta$-di-ethylamine-2,6-acetoxylidide, available from the Astra Chemical Co.), may be employed at a level of up to about 20 mg/c.c., or even more.

It is not intended that the dosage regimens of the compounds be limited to any particular range. The dosage range desired in this invention is that range necessary to accomplish the desired end of lowering serum lipid levels. The amount of lipid level reduction desired will not be the same for all patients, but depends on such factors as initial lipid level, predominance of one form of lipid over another, etc. The dosage, whether oral or parenteral must, therefore, of necessity be individually determined by the physician or veterinarian. Likewise the concentration range of the compounds in the various formulations of this invention is not limited. The concentration should be high enough to avoid an excessive number of administrations per day, but low enough to allow flexibility in administration.

Administration of the compounds of this invention by the oral route is preferred. Preferred daily dosages can be as low as 10 mg. for a human. There is, of course, no clear cut upper dosage limit since the compounds are generally non-toxic and have no untoward side effects. The maximum amount that can be taken must therefore be limited only be physical limitations on the quantity of non-nutritional material that can be digested. A convenient upper limit is about 60 grams per person per day. A preferred range of daily dosage is about 0.5 to 7.5 grams. In terms of body weight preferred dosages are from 0.8 to 1000 mg. per kg. of body weight per day with a preferred range of about 5 to 125 mg. per kg. of body weight per day. The daily dosage is preferably administered from one to four or five times daily in amounts of from about 10 mg. to about 2000 mg., and these amounts may be administered in dosage units containing at least 0.5 mg. of the compound. For example, when administrating the compound in tablet form several tablets containing from, say 0.5 to 25 mg. of active compound can be administered, up to 4 or more times daily. Alternatively, larger dosage units containing more of the compound, say 25 to 500 mg., can be administered at less frequent intervals.

For parenteral applications daily dosages of from about one-half to about one-tenth of the oral dosages are preferred. Thus daily dosages can be as low as 1.0 mg. for a human or about 0.02 mg. per kg. of body weight. The maximum dosage is determined only by physical limitations. A convenient upper limit is about 6 grams. From about 0.5 to about 1000 mg. per injection (dosage unit) in concentrations of about 0.5 to 200 mg./c.c., with from 1 to 3 injections of from 1 c.c. to 10 c.c. daily will give the required amount. Preferred formulations will contain from 5 to about 150 mg./c.c. to be given in one injection of from 1 c.c. to 5 c.c.

Larger or smaller doses can be used and, in some cases, might be preferred in individual cases. Likewise administration need not be on a daily basis, although this is preferred, but may be, for example, on alternate days or even weekly and the like. With either oral or parenteral use, a daily regimen is preferred. However, even a single administration has some effects.

Typical formulations of this invention are described in the following examples in which all parts are by weight. The compounds in the examples will have the designations given below.

I. 4,4'-ethylenebis(2,6-di-tert-butylphenol)

II. di(2,6-di-tert-butyl-p-cresol) ether
III. $\alpha,\alpha'$-ethylenedioxybis(2,6-di-tert-butyl-p-cresol)
IV. 4,4-bis(3,5-di-tert-butyl-4-hydroxyphenyl)valeric acid
V. 4,4'-bis(2,6-di-tert-butylphenol)
VI. $\alpha,\alpha'$-thiobis(2,6-di-tert-butyl-p-cresol)
VII 4,4'-thiobis(2,6-di-tert-butylphenol)
VIII. 2,2'-sulfinylbis(6-tert-butyl-p-cresol)
IX. 2,2'-thiobis(6-tert-butyl-4-chlorophenol)
X. 2,2',6,6'-tetrakis($\alpha$-methylbenzyl)-p,p'-biphenol
XI. 2,2'-di-tert-butyl-6,6'-diisopropyl-p,p'-biphenol
XII. 4,4'-thiobis(6-tert-butyl-m-cresol)
XIII. 2,2'-thiobis(6-tert-butyl-4-methoxyphenol)
XIV. 4,4-bis(5-tert-butyl-4-hydroxy-m-tolyl)valeric acid
XV. 2,2'-thiobis(6-tert-butyl-p-cresol)

EXAMPLE 1

Compound I is compressed into tablets of 10 mg. each which can be administered orally as antihypercholesterolemic agents.

EXAMPLE 2

Five hundred mg. of Compound II are mixed with 100 mg. of lactose and filled into a No. 2 hard gelatin capsule.

EXAMPLE 3

Fifty gms. of Compound III, 10 gms. of calcium sulfate and 25 gms. of sucrose are thoroughly mixed and granulated with hot 10 percent gelatin solution. The wetted mass is passed through a No. 16 U.S. standard mesh screen directly onto drying trays. The granules are dried at 120° F. and passed through a No. 20 U.S. standard mesh screen. These granules are then mixed with 15 gms. starch, 5 gms. talc and 3 gms. stearic acid, passed through a No. 60 U.S. standard mesh screen and then compressed into tablets containing 150 mg. of active ingredient.

EXAMPLE 4

Seventy-five mg. of Compound IV are mixed with 225 mg. of peanut oil to a thick slurry and filled into a soft gelatin capsule.

EXAMPLE 5

An oral composition is prepared as follows:

To 125 gms. of placebo granules composed of 64 percent lactose and 36 percent starch are added 100 gms. of Compound V. Fifteen gms. of talc and 10 gms. of magnesium stearate are added. Tableting is done on a rotary machine.

EXAMPLE 6

Linguets are obtained by combining the following components:

| | |
|---|---|
| Compound VI, mg. | 25 |
| Lactose, mg. | 50 |
| Confectioner's sugar, mg. | 60 |
| Stearin, mg. | 2 |
| Talc, mg. | 13 |

EXAMPLE 7

To a mixture of 140 gms. of Compound VII and 33.7 gms. of corn oil are added 3 gms. of gum acacia and 1.5 gms. of gum tragecanth. To the thoroughly triturated mixture is added slowly with stirring a solution of 0.1 gms. of a cetyl alcohol polyoxyethylene condensate, 40 gms. of cane sugar, 0.03 gms. of propyl-p-hydroxybenzoate, 0.3 gms. of methyl-p-hydroxybenzoate, 0.002 gm. of edible dyestuff and 110 gms. of water. After the incorporation of a suitable flavoring agent, such as imitation wild cherry, the mixture is homogenized by passage through a conventional homogenizer and there is thus obtained an emulsion suitable for oral administration in accordance with the present invention. The emulsion is bottled in half-pint bottles.

EXAMPLE 8

One hundred gms. of Compound VIII are added to a solution of 15 gms. of calcium cyclamate, 2 gms. of a condensation product of octylcresol with 8–10 molecular proportions of ethylene oxide, 3 gms. of polyvinyl pyrrolidone and 0.9 gms. of methyl-p-hydroxybenzoate in 100 gms. of water. The mixture is ball milled for several hours whereupon there is obtained a suspension suitable for oral administration in accordance with the present invention.

EXAMPLE 9

Ten gms. of Compound IX are dissolved in a mixture of 83 gms. of water, 250 gms. glycerol and 125 gms. of ethyl alcohol. To the resultant solution is added a solution of 300 gms. of sucrose and 150 gms. of water. By the incorporation of a suitable flavoring agent and coloring material there is obtained a syrup suitable for oral administration in accordance with the present invention.

EXAMPLE 10

Twenty-five gms. of sodium glycerophosphate, 25 gms. of calcium glycerophosphate and 50 gms. of Compound X are intimately mixed. The mixture is added gradually to 900 gms. of soluble casein in a conventional mixer and mixed until homogenous. There is thus obtained a dietary supplement suitable for oral administration in accordance with this invention.

EXAMPLE 11

An intimate mixture is prepared with conventional mixing equipment of 3 gms. of pyridoxine hydrochloride, 100 gms. of nicotinic acid, 100 gms. of nicotinamide, 5 gms. of methionine, 15 gms. of choline bitartrate, 150 gms. of ascorbic acid, 5 gms. of calcium pantothenate, 10 gms. of riboflavin and 1000 gms. of Compound XI. The mixture is filled with capsules which are then suitable for oral administration in accordance with this invention.

EXAMPLE 12

Three hundred and eighty-two gms. of propylene glycol are agitated for 1 hour while saturating with nitrogen gas. Twelve and four-tenth gms. of Compound XII are then added and the mixture is stirred for 30 minutes more. Then 95 c.c. of nitrogen saturated water is slowly added. After 5 minutes of further stirring 7.85 c.c. of monoethanolamine is added. Throughout the addition of ingredients the temperature is maintained below 30° C. by cooling as required. Solution is completed by stirring under nitrogen. The resulting 500 c.c. of clear, light-colored solution contains approximately 50 mg./c.c. of Compound XII and is slightly alkaline. It is subdivided and samples are filled under nitrogen into 10 c.c. multi-dose vials sealed with butyl rubber stoppers. Three c.c. doses can be withdrawn in the standard manner, by piercing the stopper with a hypodermic needle, injecting air and withdrawing the solution into the syringe. In this manner parenteral doses containing 150 mg. of Compound XII are provided.

Following the procedure of Example 12, pharmaceutical solutions suitable for intravenous and intramuscular administration are prepared according to the following formulations and packaged under nitrogen.

EXAMPLE 13

| Compound XIII, gms. | 66.6 |
| Monoethanolamine, c.c. | 22.1 |
| Lidocaine, gm. | 10 |
| Propylene glycol, gm. | 275 |
| Water to make 400 c.c.'s | |

The above solution contains 150 mgs./c.c. of Compound XIII and can be administered intramuscularly in 1 c.c. doses, once a day, giving a daily dosage of 150 mgs.

EXAMPLE 14

| Glycerine, U.S.P., liter | 1 |
| Compound XIV, gms. | 10 |
| Glycerine, U.S.P., to make 2 liters | |

The above solution contains 5 mgs./c.c. of Compound XIV and can be administered intravenously in three 1 c.c. dosage units to give a daily dosage of 15 mgs.

EXAMPLE 15

| Compound XV, gms. | 25 |
| Glycerine, U.S.P., to make 1 liter | |

The above solution contains 25 mg./c.c. of Compound XV.

It is to be understood that mixtures of the compounds of this invention can be used although it is preferred to use discreet compounds.

EXAMPLES 16–30

The above examples are repeated utilizing (the called for amounts) of 4,4'-thiobis(6-tert-butyl-o-cresol) in place of the active ingredients called for in those examples.

Similar dosage forms are made using 4,4'-bis(2,6-di-tert-butylphenol) as the active ingredient in the above examples so that they are analogous to Example 5 (in that they contain the ingredient of that example).

I claim:

1. A method of treating a mammal whose abnormally high plasma lipid level is to be reduced which comprises internally administering 4,4'-ethylenebis(2,6-di-tert-butylphenol) in an amount sufficient to reduce said plasma lipid level.

2. A method of treating a mammal whose abnormally high plasma lipid level is to be reduced which comprises internally administering 4,4'-thiobis(6-tert-butyl-o-cresol) in an amount sufficient to reduce said plasma lipid level.

3. A method of treating a mammal whose abnormally high plasma lipid level is to be reduced which comprises internally administering a bisphenol having the formula:

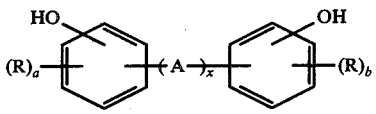

wherein: R is selected from the group consisting of alkyl having from 1-20 carbon atoms, cycloalkyl having from 6-12 carbon atoms, aryl having from 6-12 carbon atoms, and aralkyl having from 7-12 carbon atoms, $a$ and $b$ are each independently selected from 0-4; $x$ is selected from 0 and 1; and A is selected from the group consisting of —SO—, —S$_m$—, —O—CH$_2$—CH$_2$—O—, —CH$_2$SO$_2$, CH$_2$—S$_n$—CH$_2$ and CH$_2$—O—CH$_2$ and

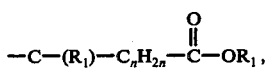

wherein $m$ is from 1-4, $n$ is from 0-4 and R$_1$ is selected from the group consisting of hydrogen and R; in an amont sufficient to reduce said plasma lipid level.

4. A method according to claim 3 wherein said compound is 4,4′-bis(2,6-di-tert-butylphenol).

5. A method for lowering serum cholesterol in animals comprising administering orally to an animal having high serum cholesterol level the compound 2,2′,6,6′-tetra-tert-butyl-p,p′-biphenol in a hypocholesteremic amount sufficient to provide a reduction in serum cholesterol content.

6. A method for lowering serum cholesterol in animals comprising administering orally to an animal a member selected from the group consisting of 4,4′-bis(2,6-di-tert-butylphenol and 2,2′-di-tert-butyl-6,6′-diisopropyl-p,p′-biphenol in an amount of from 0.8 to 1000 milligrams of compound per kilogram of animal body weight per day.

7. The method of claim 6 wherein the compound is 4,4′-bis(2,6-di-tert-butylphenol).

8. The method of claim 6 wherein the compound is 2,2′-di-tert-butyl-6,6′-diisopropylbiphenol.

9. A method for lowering serum cholesterol in an animal comprising administering orally to an animal a compound selected from the group consisting of 4,4′-thiobis(6-tert-butyl-m-cresol), 4,4′-thiobis(6-tert-butyl-o-cresol), and α,α′-thiobis(2,6-di-tert-butyl-p-cresol) in a daily dosage of from about 0.8 to about 1,000 milligrams of compound per kilogram of animal body weight.

10. A method of claim 9 which comprises administering orally to the animal a daily dosage of between about 5 to about 125 milligrams of the compound per kilogram of animal body weight.

11. The method of claim 9 wherein the compound is α,α-thiobis(2,6-di-tert-butyl-p-cresol).

12. The method of claim 9 wherein the compound is 4,4′-thiobis(6-tert-butyl-n-cresol).

13. A method for lowering serum cholesterol levels in animals comprising administering orally to an animal having a high serum cholesterol level an amount of a thiobis cresol compound effective to lower the serum cholesterol level in said animal, said thiobis cresol compound being a compound selected from the group consisting of 4,4′-thiobis(6-tert-butyl-m-cresol), 4,4′-thiobis(6-tert-butyl-o-cresol) and α,α′-thiobis (2,6-di-tert-butyl-p-cresol).

14. A method of claim 13 wherein the compound is α,α′-thiobis(2,6-di-tert-butyl-p-cresol).

15. The method of claim 13 wherein the compound is 4,4′-thiobis(6-tert-butyl-m-cresol).

16. The method of claim 13 wherein the compound is 4,4′-thiobis(6-tert-butyl-o-cresol).

* * * * *